United States Patent [19]

Lawford et al.

[11] 4,109,531
[45] Aug. 29, 1978

[54] FLUID SENSING SYSTEMS

[75] Inventors: Victor N. Lawford, Pasadena; David F. Sacarisen, Saugus, both of Calif.

[73] Assignee: International Telephone and Telegraph Corporation, New York, N.Y.

[21] Appl. No.: 814,317

[22] Filed: Jul. 11, 1977

[51] Int. Cl.² .................. G01N 9/26; G01F 23/14
[52] U.S. Cl. ........................ 73/438; 73/301; 73/706
[58] Field of Search ............ 73/32 R, 438, 395, 706, 73/299–301

[56] References Cited

U.S. PATENT DOCUMENTS

| 2,935,873 | 5/1960 | Stewart | 73/300 |
| 3,853,006 | 12/1974 | Lawford | 73/301 |
| 3,940,980 | 3/1976 | Tasker et al. | 73/395 X |

*Primary Examiner*—James J. Gill
*Attorney, Agent, or Firm*—A. Donald Stolzy

[57] ABSTRACT

A pair of vertically spaced rubber diaphragm covered bellows are employed with output means to produce a DC voltage directly proportional to the movement of the free end of one bellows. The upper bellows and diaphragm are inverted from their conventional positions. A conduit connects the two bellows together. The conduit, both bellows and both diaphragms are filled with an incompressible fluid. The fixed ends of both bellows are fixed relative to each other. This arrangement may be employed with a DC voltmeter calibrated in linear measure to indicate the level of a liquid in a storage tank. In this case, one bellows is located inside of and fixed relative to the tank at the top. The other bellows is located inside the tank at the bottom and fixed relative thereto thereat. A two bellows densitometer is also provided which may be employed with or without the liquid level system.

2 Claims, 18 Drawing Figures

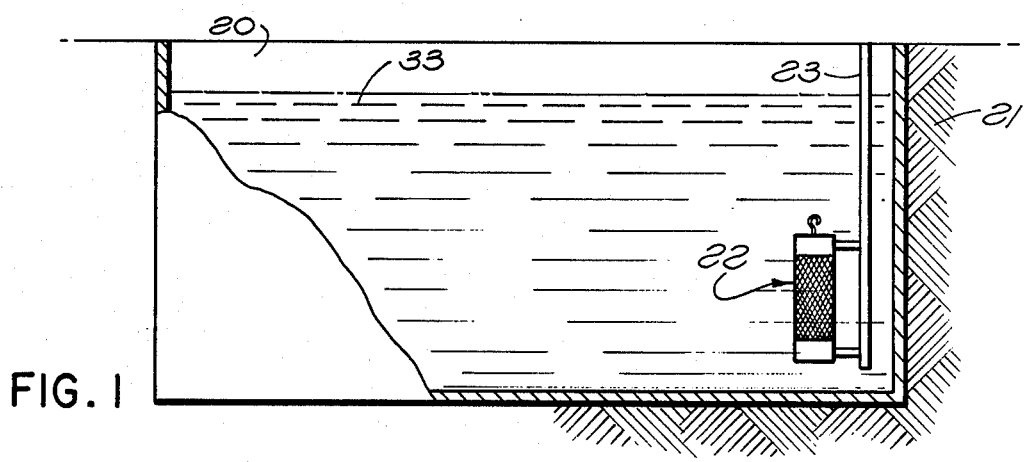
FIG. 1
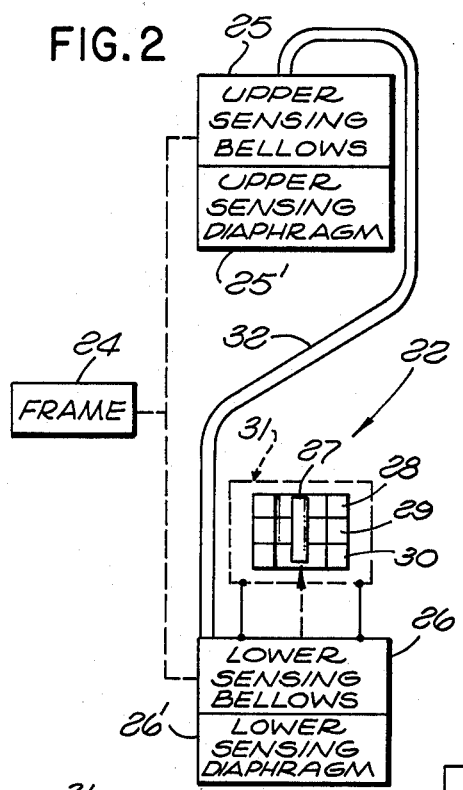
FIG. 2
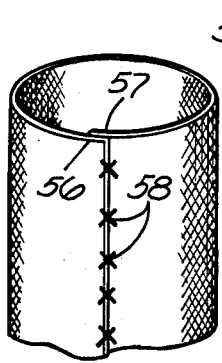
FIG. 4
FIG. 5
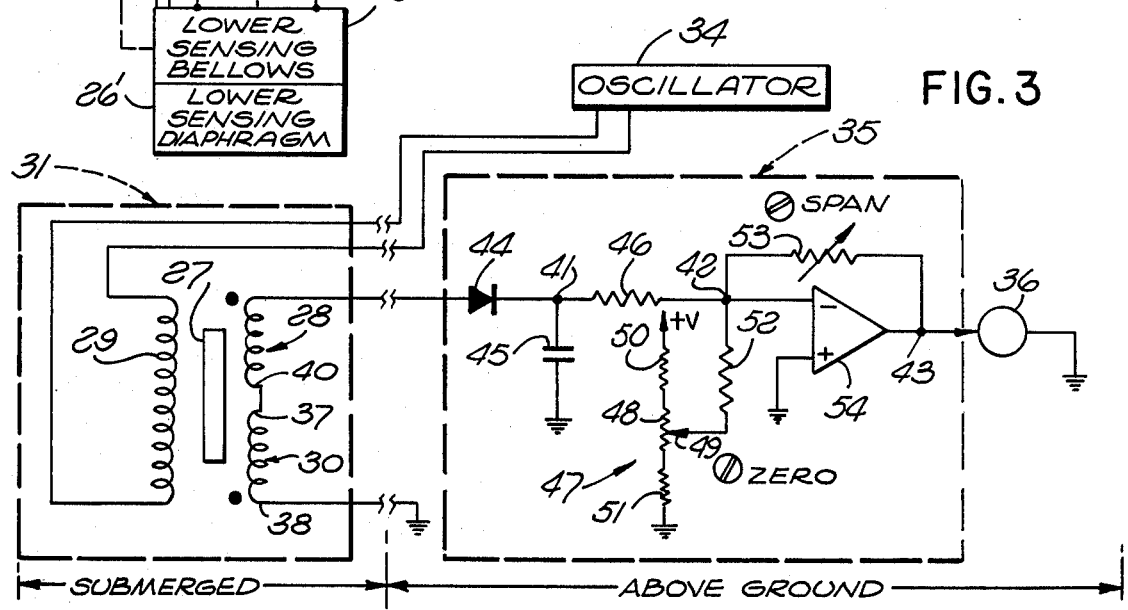
FIG. 3

FLUID SENSING SYSTEMS

BACKGROUND OF THE INVENTION

This invention relates to the fluid sensing art of the type disclosed in U.S. Pat. No. 3,853,006, issued Dec. 10, 1974, and more particularly, to systems for producing fluid level and/or fluid density analogs.

In pressurized storage or other tank systems, it is sometimes difficult or impossible to obtain accurate liquid level indications by the use of conventional devices. In many cases, the absolute tank pressure may be lower or higher than ambient. Many conventional liquid level indicators are influenced by the tank pressure when it is not the same as the ambient. For this reason, they give an erroneous liquid level indication.

In the prior art, relatively unsophisticated densitometers are virtually unknown. However, they are, nevertheless, badly needed. For example, it is important to monitor closely and continuously the density of drilling mud for oil wells or the like.

SUMMARY OF THE INVENTION

In accordance with the present invention, the above-described and other disadvantages of the prior art are overcome by providing a densitometer comprising: a frame; first and second means fixed relative to said frame in positions at the top and bottom thereof, respectively, said first and second means including first and second hollow shells, respectively, closed on the bottom thereof by first and second metal bellows, respectively, each of said first and second shells being sealed but having one opening thereinto, a conduit having a first end sealed through the opening in said first shell and a second end sealed through the opening in said second shell; a first incompressible fluid filling both of said shells and said conduit; first and second diaphragms partially defining fluid tight first and second spaces with said first and second bellows, respectively; second and third incompressible fluids filling said first and second spaces, respectively, said first, second and third fluids being the same or different, both of said diaphragms facing downwardly; third means connected from one of said first and second bellows to produce an electrical output signal directly proportional to the difference between the pressures at the respective locations of said first and second diaphragms, respectively; and utilization means connected from the output of said third means.

The above-described and other advantages of the present invention will be better understood from the following detailed description when considered in connection with the accompanying drawings.

BRIEF DESCRIPTION OF THE DRAWINGS

In the drawings which are to be regarded as merely illustrative:

FIG. 1 is a vertical sectional view of a drilling mud tank for an oil well with a densitometer probe of the present invention suspended therein;

FIG. 2 is a diagrammatic view of the densitometer probe shown in FIG. 1;

FIG. 3 is a schematic diagram of a drilling mud densitometer constructed in accordance with the present invention;

FIG. 4 is a broken away perspective view of expanded metal rolled into a cylinder and tacked together;

FIG. 5 is an elevational view of the expanded metal;

DESCRIPTION OF THE PREFERRED EMBODIMENTS

Figure 6:
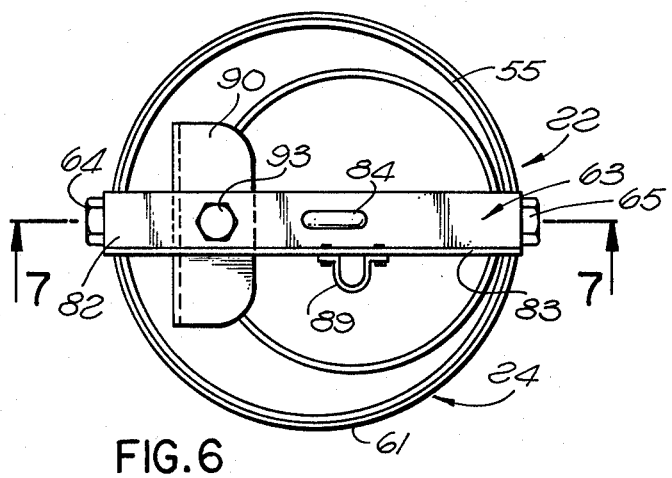
FIG. 6 is a top plan view of the mud densitometer probe shown in FIGS. 1 and 2.

In FIG. 1, a drilling mud tank for an oil well is illustrated at 20 supported in the earth at 21. A drilling mud densitometer probe 22 is mounted on a support 23 fixed relative to a portion of the tank 20. As shown in FIG. 2, probe 22 has a frame 24. Upper and lower sensing bellows 25 and 26, respectively, and upper and lower sensing diaphragms 25' and 26', respectively, are provided, all of which generally have fixed ends fixed relative to frame 24. The free end of upper bellows 25 and the free end of upper diaphragm 25' are free to move responsive to the pressure at their location. As the free ends of the lower bellows and diaphragm 26 and 26' move, they also move a ferromagnetic sleeve 27 relative to transformer windings 28, 29 and 30 in a transducer 31. Windings 28, 29 and 30 are fixed relative to frame 24. A tube 32 connects the interiors of both the upper and lower bellows 25 and 26. The free end of the lower bellows 26 thus moves in response to the difference between the pressures at the respective locations of the free ends of the upper and lower bellows 25 and 26. Windings 28, 29 and 30 are connected in a manner to produce an output signal which is directly proportional to the said differential pressure. This signal, when displayed on a voltmeter or ammeter, can indicate the density of drilling mud 33 shown in the tank 20 in FIG. 1. The interiors of bellows 25 and 26 and the interior of the tube 32 may be filled with any conventional incompressible fill fluid.

Transducer 31 may be as shown in FIG. 3. Alternatively, transducer 31 may be any conventional position transducer. In FIG. 3, windings 28, 29 and 30 are again shown with sleeve 27.

Transducer 31 is submerged. An oscillator 34, an output circuit 35 and a voltmeter 36 are provided above the earth's surface. The output of oscillator 34 is connected across winding 29. Windings 28 and 30 are connected in series in voltage bucking relation. The output of the series connection of windings 28 and 30 is impressed upon output circuit 35. The output of circuit 35 is impressed upon voltmeter 36. Voltmeter 36 may be calibrated in drilling mud density, if desired. For example, voltmeter 36 may be calibrated in pounds per gallon. Alternatively, voltmeter 36 may be calibrated in percent, specific gravity or in other measure, if desired.

Output circuit 35 may be entirely conventional, if desired. Winding 30 has ends 37 and 38. Winding 28 has ends 39 and 40. Winding ends 37 and 40 are connected together. Winding end 38 is grounded.

Output circuit 35 has various junctions 41, 42 and 43 therein. A diode 44 is connected from winding end 39 to junction 41 and poled to be conductive toward junction 41. A capacitor 45 is connected from junction 41 to ground. A resistor 46 is connected between junctions 41 and 42.

A potentiometer is provided at 47 having a winding 48 and a wiper 49. A resistor 50, winding 48 and a resistor 51 are connected in succession in that order in series from potential + V to ground. A resistor 52 is connected from junction 42 to wiper 49. A feedback resistor 53 is connected between junctions 42 and 43. A conventional differential amplifier 54 is also provided which has an inverting input connected from junction 42 and a noninverting input which is grounded. Amplifier 54 also has an output connected to junction 43, junction 43 being connected to one side of voltmeter 36. The other side of voltmeter 36 is grounded.

The position of wiper 49 on winding 48 of potentiometer 47 may be adjusted so that voltmeter 36 will correctly read zero density. Resistor 53 is a variable resistor which may be adjusted so that the full scale reading of voltmeter 36 will be accurate.

A portion of the frame 24 in FIG. 2 of probe 22 is shown in FIG. 4 including expanded metal which is rolled into a cylinder 55 having contiguous edges 56 and 57 held in place by arc welds at 58. An enlarged view of a portion of cylinder 55 is shown in FIG. 5 including a lattice work 59 defining diamond-shaped interstices 60.

Alternatively, density may be detected in accordance with the present invention by the use of a strain gage analog transducer.

Figure 11:
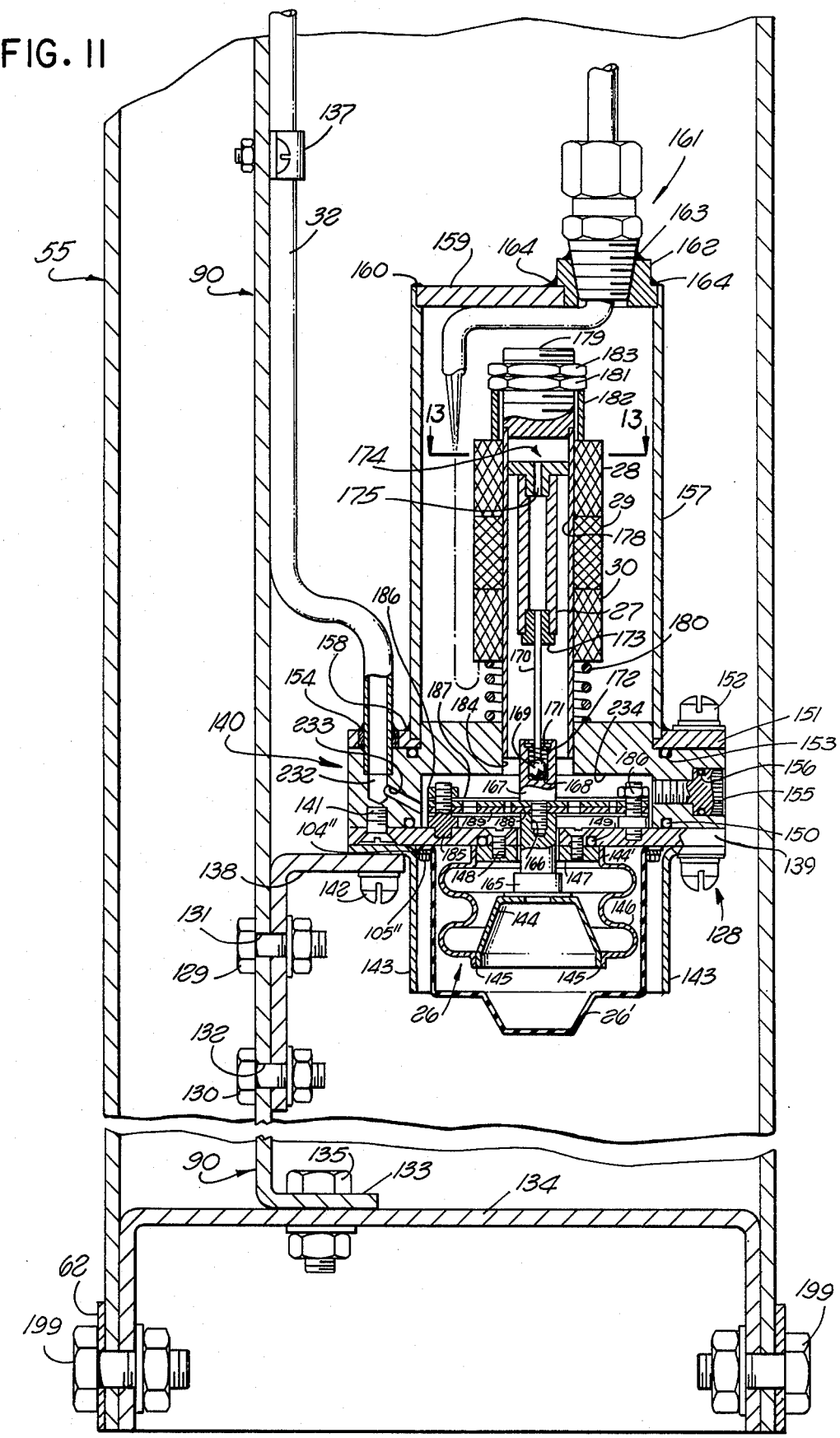
FIG. 11 is a vertical sectional view of a lower portion of the mud densitometer probe taken on the line 7—7 shown in FIG. 6.

Probe 22, including frame 24, is illustrated in a plan view in FIG. 6. Probe 22 includes the expanded metal cylinder 55. The interstices in metal cylinder 55 and cylinder 55 itself are not illustrated in some places in drawings for clarity. Rings or bands 61 and 62 are provided around the uppermost and lowermost portions of cylinder 55, as shown in FIGS. 6, 7 and 11.

As shown in FIG. 6, an angle iron 63 is fixed to cylinder 55 by two bolts 64 and 65.

Figure 7:
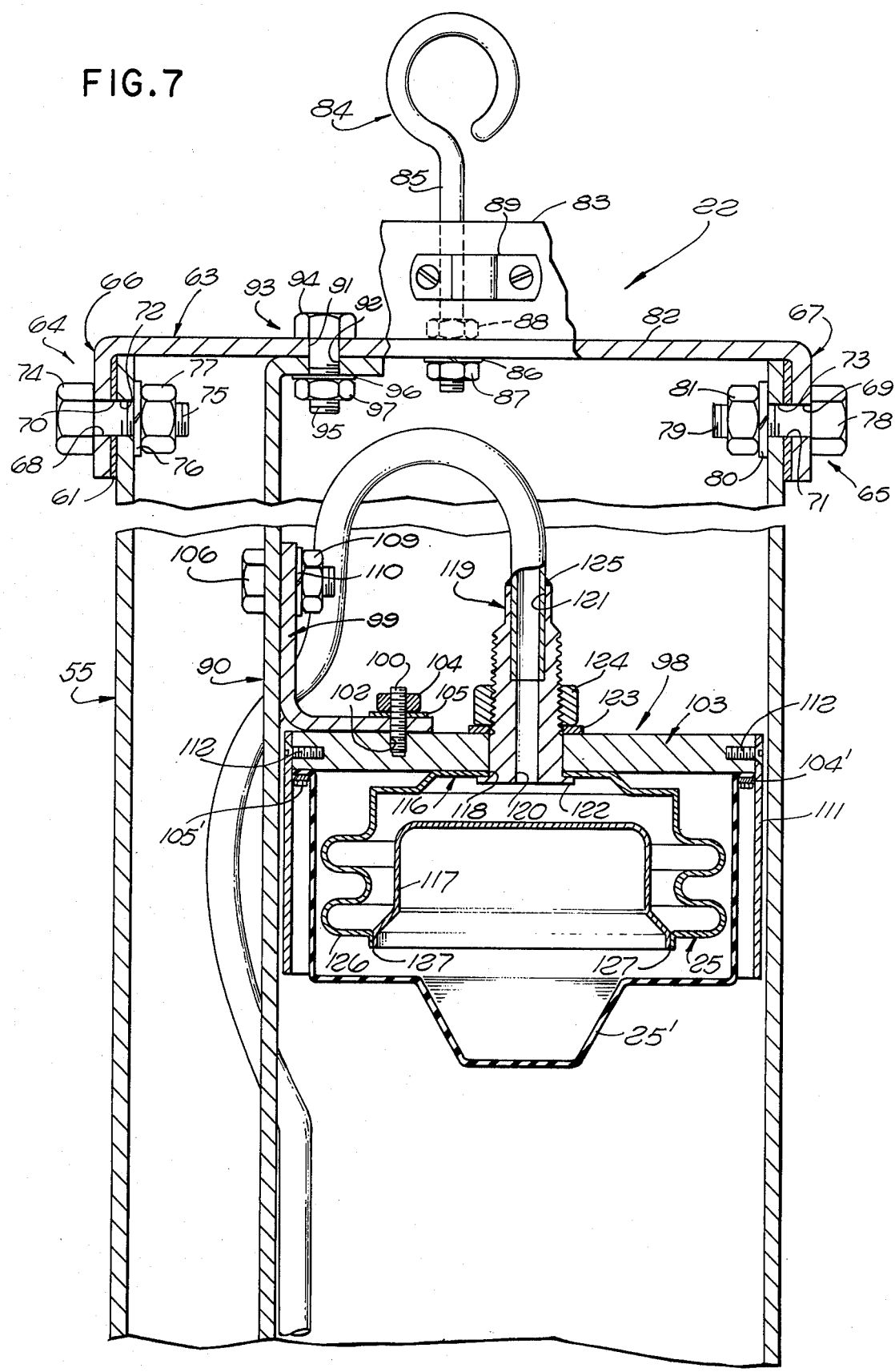
FIG. 7 is a vertical sectional view of the upper portion of the probe taken on the line 7—7 shown in FIG. 6.

As shown in FIG. 7, angle iron 63 has downwardly projecting portions 66 and 67. Portion 66 has a hole 68 therethrough. Portion 67 has a hole 69 therethrough. Band 61 has a hole 70 which lies in registration with hole 68, and a hole 71 which lies in registration with hole 69. Cylinder 55 has a hole 72 therethrough which lies in registration with band hole 70, and a hole 73 which lies in registration with band hole 71.

Bolt 64 has a head 74 and a shank 75 which projects through the holes 68, 70 and 72. A lock washer 76 is positioned around bolt shank 75. A nut 77 is threaded to bolt shank 75. Similarly, bolt 65 has a head 78 and a shank 79 that projects through the holes 69, 71 and 73. A lock washer 80 is positioned around bolt shank 79. A nut 81 is threaded to bolt shank 79.

Angle iron 63 has a horizontal portion 82 and a vertical portion 83. A hook may be provided at 84 that has a shank 85 that is slidable through a hole in angle iron portion 82, not shown. Hook 84 is fixed relative to angle iron portion 82 by a lock washer 86, and nuts 87 and 88 threaded to hook shank 85. See also FIG. 6.

As shown in FIG. 6, a conventional electrical conduit bracket 89 is bolted to angle iron portion 83. Bracket 89 holds the conduit which carries the four electrical leads which extend from transducer 31 to above the surface of the ground, as illustrated in FIG. 3.

The bellows 25 and 26 are fixed relative to a bracket 90, as shown in FIG. 6. Bracket 90 is also shown in FIGS. 7, 9 and 11.

As shown in FIG. 7, angle iron portion 82 has a hole 91 therethrough. Bracket 90 has a hole 92 therethrough that lies in registration with hole 91. A bolt 93 is provided with a head 94 and a shank 95 which projects through holes 91 and 92. A lock washer 96 is provided around shank 95. A nut 97 is threaded to shank 95.

As shown in FIG. 7, a bellows assembly 98 is fixed to bracket 90 by a bracket 99. A rubber or rubber-like, metal or other diaphragm 25' is sealed to a plate 103 by a ring 104' and cap screws 105'. Diaphragm 26' is sealed to plate 139 by a ring 104" and cap screws 105". Two studs 100 are slidable through two corresponding holes 101 in bracket 99. See FIG. 8. Each stud 100 if fixed relative to and/or threaded in a corresponding recess 102 in plate 103. A lock washer 105 is positioned around each stud 100. A nut 104 is threaded to each stud 100 to hold bracket 99 in place.

Figure 8:
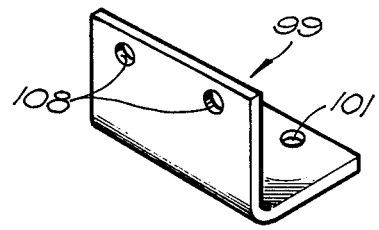
FIG. 8 is a perspective view of a bracket shown in FIG. 7.
Figure 9:
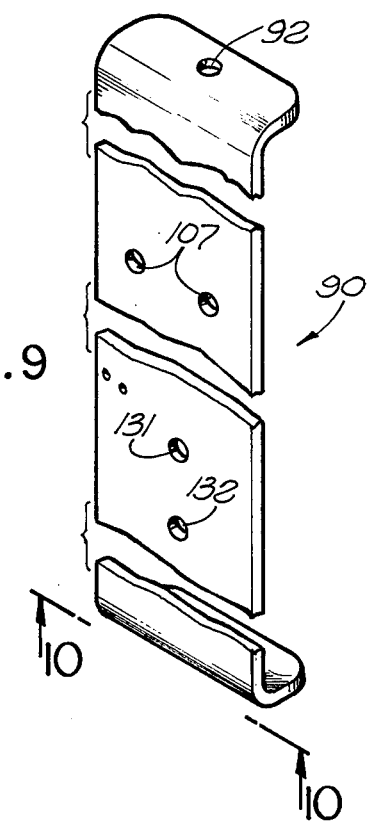
FIG. 9 is a broken perspective view of another bracket shown in FIG. 7.

Bracket 99 is fixed to bracket 90 by two bolts 106 that extend through two corresponding holes 107 in bracket 90, as shown in FIG. 9, and through two other corresponding holes 108 in bracket 99, as shown in FIG. 8. Bolts 106 are provided with nuts 109 and lock washers 110, as before.

In FIG. 7, a cylinder 111 may be fixed to plate 103 by any conventional means such as four or more countersunk screws 112.

The chambers formed inside of and outside of bellows 25 and 26 may be filled with ethylene glycol or some other conventional fill fluid or one or more may be filled with different fill fluids.

In FIG. 7, bellows 25 is shown having a fixed end 116 and a free end 117. End 116 is fixed relative to plate 103. End 116 is provided with an opening 118 through which a projection 119 extends. Projection 119 has a hollow interior with a bore 120, and a counterbore 121. Projection 119 also has a flange 122 which rests on and holds bellows end 116 tight to plate 103. A lock washer 123 is provided around projection 119. A nut 124 is threaded to the exterior of projection 119 and holds flange 122 tightly against bellows end 116. Tube 32 may be provided with a fluid tight seal to projection 119 at 125, if desired. Seal 125 may be a weld, if desired.

Free end 117 of bellows 25 may be heliarc welded to corrugations 126, if desired, at 127.

As shown in FIG. 11, a bellows assembly 128 is mounted on bracket 90 by bolts 129 and 130, as before. The holes for bolts 129 and 130 in bracket 90 are illustrated at 131 and 132, respectively, both in FIGS. 9 and 11.

Figure 10:
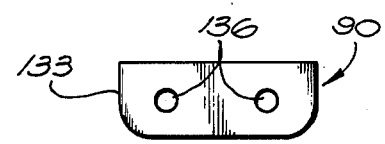
FIG. 10 is a bottom plan view of the bracket shown in FIG. 9.

As shown in FIG. 11, bracket 90 has a horizontal portion 133 which is fixed to a cylindrical cup 134 by two bolts 135. The bolts 135 extend through holes 136, as shown in FIG. 10.

As shown in FIG. 11, tube 32 connects both assemblies 98 and 128. Tube 32 is fixed intermediate its ends to bracket 90 by a conventional pipe clamp 137.

Bolts 129 and 130 fix a bracket 138 relative to bracket 90.

Assembly 128 includes plate 139 which is fixed to a block 140 preferably by three or more countersunk screws 141. Preferable, the same number of screws 142 fix a cylindrical guard 143 to plate 139 and/or block 140.

Preferably, but not necessarily, the number of screws 142 equals the number of screws 141. Each screw 142 is then positioned midway between each screw 141. Guard 143, plate 139 and block 140 may thus be generally circular. Bellows 26 includes a free end 144 and a fixed end 144'. Preferably, free end 144 is heliarc welded at 145 to corrugations 146. Fixed end 144' is preferably sealed in a fluid tight manner to a ring 147. Ring 147 is fixed to plate 139 by screws 148. An O-ring seal 149 is provided between ring 148 and plate 139. An O-ring seal 150 is also provided between plate 139 and block 140. A ring is provided around the top of block 140 at 151. Ring 151 is held to block 140 by preferably three or more screws 152. An O-ring seal 153 is provided between ring 151 and block 140.

Tube 32 is provided with a conventional fluid tight seal to ring 151 at 154. The seal at 154 also seals tube 32 to block 140. Block 140 has a fill plug 155 with an O-ring seal at 156. A cylinder 157 is sealed at 158 to ring 151. A cover 159 for cylinder 157 is sealed thereto at 160. An entirely conventional electrical conduit connector is provided at 161 threaded into an insert 162 in cover 159. Seals are then provided at 163 and 164.

The four leads passing through connector 161 then are connected to coils 28, 29 and 30, shown in FIG. 11 in the manner shown in FIG. 3.

A solid shaft 165 is fixed in a fluid tight manner to bellows end 144. Shaft 165 has a threaded hole 166 in the upper end thereof into which a member 167 is threaded. Member 167 has a recess 168 thereinto in which a ball 169 is positioned. A shaft 170 is fixed to ball 169. Ball 169 is loose in recess 168 and can rotate about its center. A snap ring 171 holds a spring 172 against ball 169.

Figure 12:
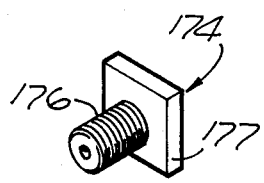
FIG. 12 is a perspective view of a component part of the assembly of FIG. 11.
Figure 13:
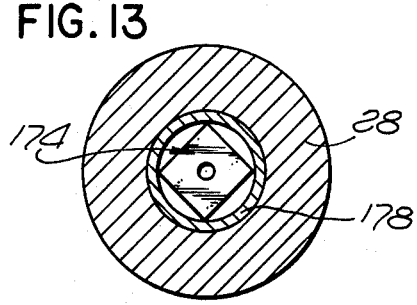
FIG. 13 is a transverse sectional view of the assembly of FIG. 11 taken on the line 13—13 therein.
Figure 16:
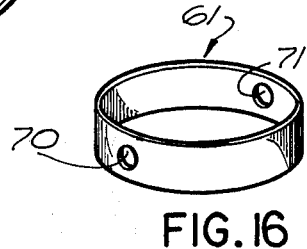
FIG. 16 is a perspective view of a bracing cup for the expanded metal of the densitometer frame.

A ferrule 173 is threaded to sleeve 27 and is fixed thereto and to shaft 170. A ferrule 174 is also fixed to sleeve 27. Ferrule 174 has a breather hole 175 through the center thereof. If desired, ferrule 174 may have a threaded shank 176, as shown in FIG. 12. The head of ferrule 174 is square, as shown at 177 in FIG. 12. Head 177 can, therefore, slide in a tube 178 which surrounds it, as shown in FIGS. 11 and 13.

As shown in FIG. 11, a threaded plug 179 is fixed to and sealed over the upper open end of tube 178. A spring 180 surrounds tube 178 and urges windings 28, 29 and 30 in an upward direction, as viewed in FIG. 11. The position of windings 28, 29 and 30 may be adjusted by the use of a nut 181 threaded to plug 179. A ring 182 loosely surrounds plug 179 and tube 178. A lock nut 183 is threaded to plug 179. Tube 178 is sealed to a bore 184 through block 140.

Figure 14:
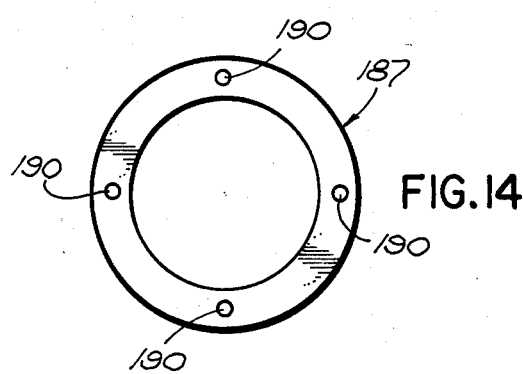
FIG. 14 is a top plan view of a mounting ring shown in FIG. 11.
Figure 15:
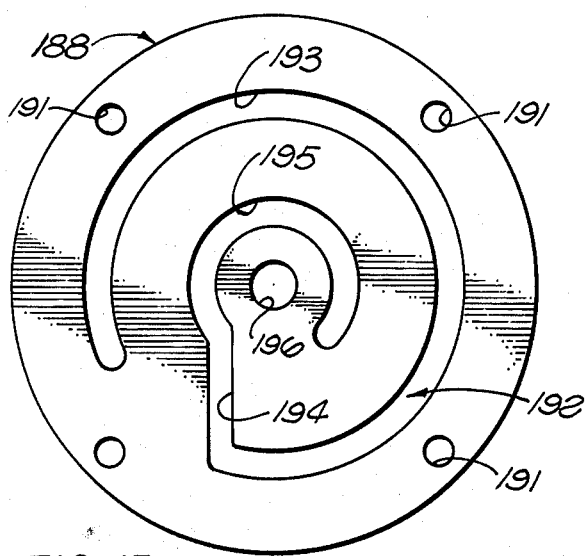
FIG. 15 is an enlarged top plan view of a spring shown in FIG. 11.

Four studs are provided at 185 which are threaded into plate 139 symmetrically about the axis of shaft 165. The studs 185 are provided with nuts 186 to clamp, with a ring 187, two springs 188 and 189 in place. Ring 187 is shown in FIG. 14 having holes 190 for studs 185. One or more springs 188 and 189 may be provided. All these springs may be identical except for thicknesses. An enlarged top plan view of one such spring is shown in FIG. 15. In FIG. 15, spring 188 is provided with holes 191 that are placed in registration with holes 190 (FIG. 14). Spring 188 also has a slot 192 with various portions 193, 194 and 195. Spring 188 also has a circular hole 196 therethrough through which the lower portion of member 167 is slidable. However, both springs 188 and 189 are actually clamped between member 167 and shaft 165.

Any conventional springs may be employed for springs 188 and 189. A rubber, rubber-like, metal or other diaphragm 143' is provided inside a guard 143.

As shown in FIG. 11, band 62, cylinder 55 and cup 134 are fixed together by bolts 199, as before.

Note will be taken in FIG. 7 that bellows end 117 is sealed to corregations 126. Bellows end 116 is also sealed to flange 122 of projection 119. Projection 119 is sealed around tube 32 at 125. Tube 32 is sealed to block 140 at 154 in FIG. 11. Fluid flow can exist into and out of tube 32 at its lower end from and to a recess 232 in block 140. A passageway 233 connects a recess 234 in block 140 with recess 232. An incompressible fluid can then occupy the space inside tube 178 and inside and outside bellows 26. A fluid tight seal is provided between tube 178 and the hole 184 through block 140. Plug 179 provides a fluid tight seal at the upper end of tube 178. The upper end of bellows 26 at 144' is fixed to ring 147 in a fluid tight manner. Corregations 146 are fixed to bellows end 144 at 145 in a fluid tight manner. A conventional silicon oil may fill the chambers both inside and outside of both bellows 25 and 26, and the tube 32.

The system of the present invention may be used as a liquid level detector as well as a densitometer, each for any fluid. Liquid level detectors constructed in accordance with the present invention are shown in both FIGS. 17 and 18.

Figure 17:
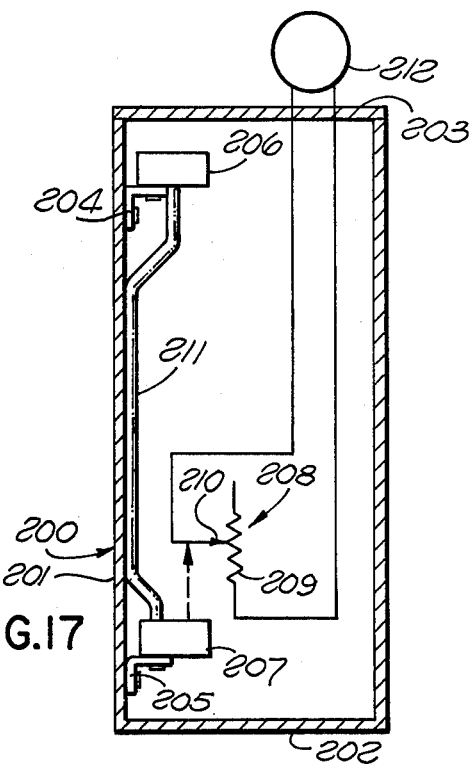
FIG. 17 is a diagrammatic view of another embodiment of the present invention.

In FIG. 17, a tank to hold a liquid is indicated at 200. The tank is shown having a cylindrical wall 201, a circular bottom wall 202 and a circular top wall 203. The tank 200 may be completely sealed, if desired. Alternatively, the tank 200 need not be sealed. Brackets 204 and 205 fix bellows assemblies 206 and 207, respectively, at the top and bottom of the tank 200, respectively. The transducer 208 is provided including a potentiometer having a winding 209 and a wiper 210. The position of wiper 210 on winding 209 is varied directly to the position of the movable end of the bellows in the assembly 207. Upper and lower bellows assemblies 206 and 207 may be identical to upper and lower bellows assemblies 98 and 128 shown in FIGS. 7 and 11, respectively. Assemblies 206 and 207 may be connected with a tube 211 similar to tube 32.

Outside the tank 200, an ohmmeter 212 calibrated in linear measure or volume measure or percent full may be connected to read the resistance of potentiometer winding 209 from wiper 210 to one end of the winding 209.

Figure 18:
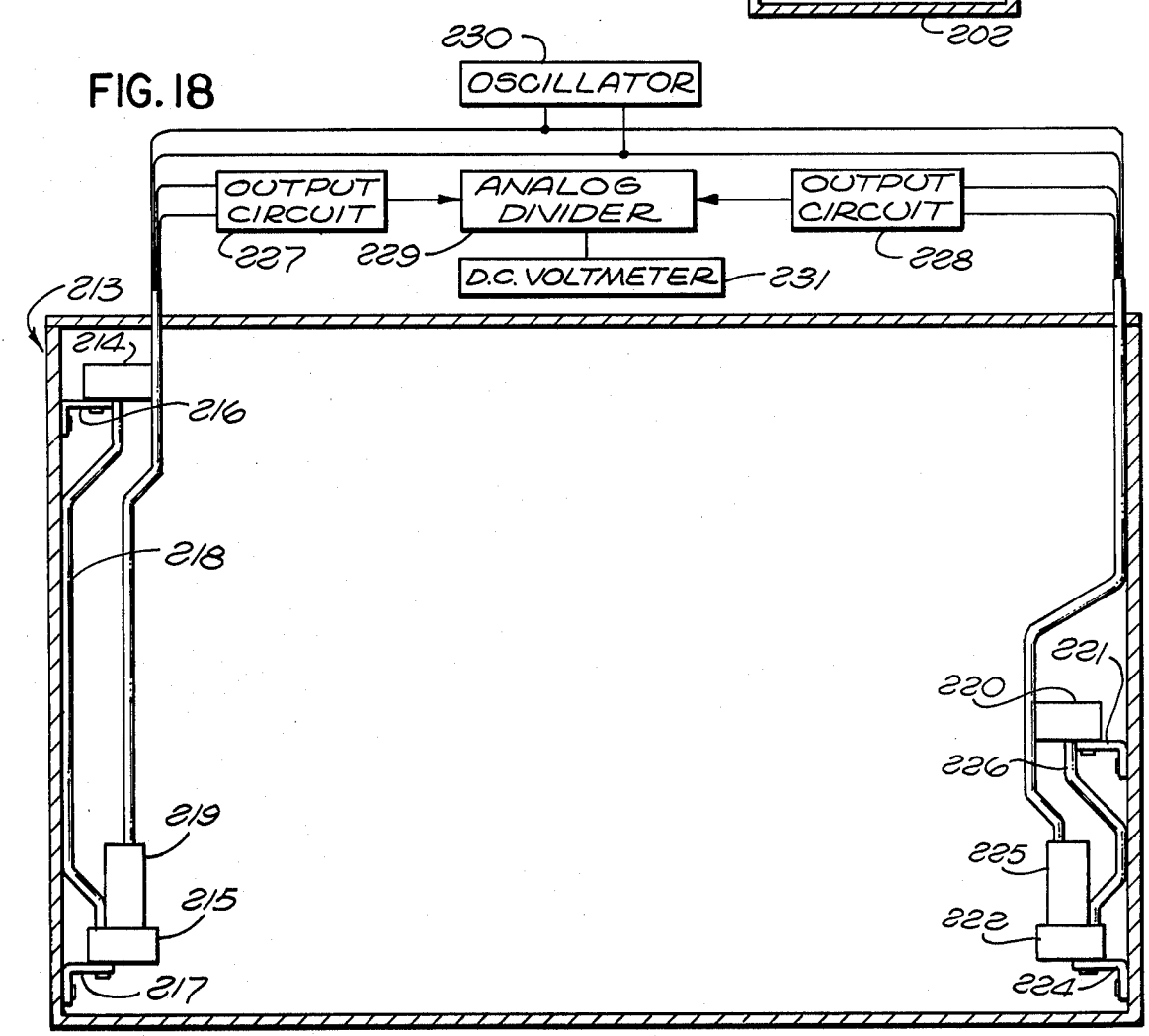
FIG. 18 is a diagrammatic view of still another embodiment of the present invention.

Another liquid level system is shown in FIG. 18. The system of FIG. 17 is not adapted to read liquid level for liquids of two or more different densities. The system of FIG. 18 can properly read the liquid level of liquids of any number of densities. A tank 213 is provided in FIG. 18 which may be identical to tank 200, if desired. Upper and lower bellows assemblies 214 and 215 are fixed relative to tank 213 by brackets 216 and 217, respectively. Assembly 214 is fixed relative to tank 213 at the bottom thereof. A tube 218, which may be similar to tube 32, connects the assemblies 214 and 215. A transducer 219 is employed which may be identical to transducer 31. Tank 213 may have a height considerably greater than that shown in FIG. 18 in relation to its diameter.

An auxiliary bellows assembly 220 is fixed relative to tank 213 a short distance above the bottom thereof by a bracket 221. A lower bellows assembly 222 is fixed relative to tank 213 at the bottom thereof by a bracket 224. A transducer 225 is employed which may be identical to transducer 219. A tube 226, identical to tube 32, connects assemblies 220 and 222. Output circuits 227 and 228 are connected from the respective transducers 219 and 225 to an analog divider 229. An oscillator 230 is connected to both of the transducers 219 and 225. A DC voltmeter calibrated in linear or volume measure is indicated at 231 connected from the output of divider 229. Divider 229 divides the output of circuit 227 by the output of circuit 228.

In FIG. 18, for voltmeter 231 to read liquid level accurately, bellows assembly 220 must at all times be submerged in the liquid contained by tank 213.

In FIG. 18, note will be taken that height is equal to pressure divided by density. The output of circuit 227 thus is a pressure analog. The output of circuit 228 is a density analog. Divider 229 divides the pressure analog by the density analog. Divider 229 then impresses this quotient on voltmeter 231.

The phrase "utilization means" is hereby defined for use herein to include, but not be limited to, an automatic refill system, a visual indication or otherwise.

All the tank level systems disclosed herein may or may not, as desired, incorporate indicators indicating percent full, volume measure or linear measure, or other measure.

Oscillator 34, shown in FIG. 3, and oscillator 230, shown in FIG. 18, may be entirely conventional. Transducer 31, output circuit 35 and voltmeter 36 may all be entirely conventional, if desired.

Ohmmeter 212 may also be entirely conventional.

In FIG. 18, divider 229 and voltmeter 231 both may be entirely conventional.

Additional fluid tight seals may be provided, if desired.

If desired, the ratio of the heights to the diameters of the tanks 200 and 213, shown in FIG. 17 and FIG. 18, respectively, may be much larger than as illustrated.

What is claimed is:

1. A densitometer comprising: a frame; first and second means fixed relative to said frame in positions at the top and bottom thereof, respectively, said first and second means including first and second hollow shells, respectively, closed on the bottom thereof by first and second bellows, respectively, each of said first and second shells being sealed but having one opening thereinto, a conduit having a first end sealed through the opening in said first shell and a second end sealed through the opening in said second shell; a first incompressible fluid filling both of said shells and said conduit; first and second diaphragms partially defining fluid tight first and second spaces with said first and second bellows, respectively; second and third incompressible fluids filling said first and second spaces, respectively, said first, second and third fluids being the same or different, both of said diaphragms facing downwardly; third means connected from one of said first and second bellows to produce an electrical output signal directly proportional to the difference between the pressure at the respective locations of said first and second diaphragms, respectively; and utilization means connected from the output of said third means.

2. The invention as defined in claim 1, wherein said utilization means includes a D.C. voltmeter calibrated in units of density.

* * * * *